United States Patent
Garrett et al.

(10) Patent No.: US 11,384,870 B2
(45) Date of Patent: Jul. 12, 2022

(54) TAPERED STRESS-RELIEVED HELICALLY REINFORCED HOSE

(71) Applicant: GLOBALMED INC., Trenton (CA)

(72) Inventors: Carl J Garrett, Beverly, MA (US); Donald K Hadley, Belleville (CA); Martin E Forrester, Trenton (CA)

(73) Assignee: GLOBALMED, INC., Trenton (CA)

( * ) Notice: Subject to any disclaimer, the term of this patent is extended or adjusted under 35 U.S.C. 154(b) by 0 days.

(21) Appl. No.: 16/377,748

(22) Filed: Apr. 8, 2019

(65) Prior Publication Data
US 2019/0234539 A1 Aug. 1, 2019

Related U.S. Application Data

(60) Division of application No. 15/530,040, filed on Nov. 22, 2016, now Pat. No. 10,584,811, which is a
(Continued)

(51) Int. Cl.
| | |
|---|---|
| *F16L 11/00* | (2006.01) |
| *F16L 11/16* | (2006.01) |
| *B29C 53/58* | (2006.01) |
| *B29C 53/60* | (2006.01) |
| *F16L 9/00* | (2006.01) |
| *F16L 11/12* | (2006.01) |
| *A61M 16/08* | (2006.01) |
| *B29D 23/00* | (2006.01) |
| *B29C 71/02* | (2006.01) |
| *F16L 11/10* | (2006.01) |

(Continued)

(52) U.S. Cl.
CPC .......... *F16L 11/16* (2013.01); *A61M 16/0875* (2013.01); *B29C 53/582* (2013.01); *B29C 53/585* (2013.01); *B29C 53/60* (2013.01); *B29C 53/607* (2013.01); *B29C 71/02* (2013.01); *B29D 23/001* (2013.01); *F16L 9/006* (2013.01); *F16L 11/10* (2013.01); *F16L 11/121* (2013.01); *A61M 2207/00* (2013.01); *B29C 2071/022* (2013.01); *B29K 2101/12* (2013.01); *B29L 2023/005* (2013.01)

(58) Field of Classification Search
CPC .. F16L 11/16; F16L 9/006; F16L 11/10; F16L 11/121
USPC .................................................. 138/122, 129
See application file for complete search history.

(56) References Cited

U.S. PATENT DOCUMENTS

| | | | | |
|---|---|---|---|---|
| 2,930,007 | A | * | 3/1960 | Anderson ................. H01P 3/14 333/241 |
| 3,122,171 | A | * | 2/1964 | Philips .................... F16L 11/16 138/129 |

(Continued)

*Primary Examiner* — James F Hook
(74) *Attorney, Agent, or Firm* — David A. Burge; Benjamin D. Burge

(57) ABSTRACT

Helically reinforced, flexible tubing or hose is formed from continuously extruded thermoplastic material helically circumferentially wound at a wrapping station around an array of bearing-supported rods that are concurrently but individually turned and are adjustably canted relative to an imaginary center axis. The tubing or hose being formed has a continuous reinforcing rib helically wound therearound and continuously integrally connected thereto. The resulting tubing or hose may be transversely severed at intervals along its length to provide discrete lengths of hose that are annealed while axially compressed to relieve stress.

12 Claims, 6 Drawing Sheets

Related U.S. Application Data continuation of application No. 13/507,172, filed on Jun. 11, 2012, now Pat. No. 9,505,164, which is a continuation-in-part of application No. 12/799,263, filed on Apr. 21, 2010, now Pat. No. 8,453,681.

(60) Provisional application No. 61/627,425, filed on Oct. 12, 2011, provisional application No. 61/335,023, filed on Dec. 30, 2009.

(51) Int. Cl.
*B29K 101/12* (2006.01)
*B29L 23/00* (2006.01)

(56) References Cited

U.S. PATENT DOCUMENTS

| | | | | |
|---|---|---|---|---|
| 3,173,172 A * | 3/1965 | Pasquetti | ............ | B29C 66/4329 29/819 |
| 3,739,815 A * | 6/1973 | Rejeski | .................. | F16L 11/24 138/122 |
| 3,824,832 A * | 7/1974 | Starostin | ................... | F28F 1/40 72/285 |
| 3,861,423 A * | 1/1975 | Hedges | ............... | F24F 13/0245 138/119 |
| 3,861,424 A * | 1/1975 | Mizutani | ................ | F16L 11/112 138/119 |
| 3,890,181 A * | 6/1975 | Stent | ........................ | B31C 3/00 156/425 |
| 3,910,808 A * | 10/1975 | Steward | ................ | B29C 53/845 156/429 |
| 3,966,525 A * | 6/1976 | Steward | .................. | B29C 53/78 156/195 |
| 4,304,266 A * | 12/1981 | Kutnyak | ................ | F16L 11/24 138/122 |
| 4,621,662 A * | 11/1986 | Olry | ...................... | D04H 18/02 138/129 |
| 5,848,223 A * | 12/1998 | Carlson | .................. | B29C 48/12 392/478 |
| 6,315,715 B1 * | 11/2001 | Taylor | .................... | A61B 1/018 138/122 |
| 8,590,576 B2 * | 11/2013 | Hagist | ................ | F02M 37/0017 138/121 |
| 8,631,830 B2 * | 1/2014 | Gosis | ..................... | F16L 47/265 138/109 |
| 2004/0079371 A1 * | 4/2004 | Gray | ................. | A61M 16/0816 128/204.17 |
| 2007/0215228 A1 * | 9/2007 | Gosis | ..................... | F16L 11/16 138/129 |
| 2009/0301593 A1 * | 12/2009 | Zucchi | ................... | F16L 11/112 138/109 |
| 2014/0102452 A1 * | 4/2014 | Forrester | ........... | A61M 16/0875 128/204.18 |

\* cited by examiner

TAPERED STRESS-RELIEVED HELICALLY REINFORCED HOSE

REFERENCE TO RELATED APPLICATIONS

This application is a division of Co-pending application Ser. No. 15/530,040 filed Nov. 22, 2016 which is a continuation of application Ser. No. 13/507,172 filed Jun. 11, 2012 now U.S. Pat. No. 9,505,164 issued Nov. 29, 2016 which is a continuation-in-part of application Ser. No. 12/799,263 filed Apr. 21, 2010 now U.S. Pat. No. 8,453,681.

REFERENCE TO PROVISIONAL APPLICATIONS

Application Ser. No. 13,507,172 referenced above claimed the benefit of the Oct. 12, 2011 filing date of application Ser. No. 61/627,425.

Application Ser. No. 12/799,263 referenced above claimed the benefit of the Dec. 30, 2009 filing date of application Ser. No. 61/335,023.

INCORPORATIONS BY REFERENCE

The disclosures and entire contents of all of the applications identified above are incorporated herein by reference.

BACKGROUND

The present invention relates to helically reinforced tubing and/or hose that has one or more characteristics that vary along at least a selected portion of the continuous length of the tubing or hose, including diametrical size, wall thickness, pitch, strength, flexibility, stiffness, helix size and weight, while one or more of these characteristics may remain substantially constant along the same or a different selected portion of the continuous length of the tubing or hose, as may be desired for use in specific applications.

Tubing and hose that has one or more characteristics (such as are mentioned above) that vary progressively along at least a selected portion of the length of the tubing or hose has many commercial, industrial and medical uses.

Commercially, for example, a length of tubing or hose that has at least a portion of its length that tapers in diameter can be used to improve air flow and reduce the accumulation of debris along the length of tubing or hose.

Industrially, for example, a length of tubing or hose that has at least a portion of its length that tapers in diameter can be used to eliminate the need for adapters and connectors between lengths of tubing or hose that need to be of different diameters for various purposes.

Medically, for example, a length of tubing or hose that has at least a portion of its length that tapers in diameter can be useful in providing breathing conduits used with sleep apnea equipment and other medical devices related to breathing.

SUMMARY

The present invention preferably makes use of tubing or hose forming techniques of the general type described in U.S. Pat. No. 3,910,808 issued Oct. 7, 1975, and U.S. Pat. No. 3,966,525 issued Jun. 29, 1976 to William L. Steward, but advances the technology significantly beyond what is disclosed or suggested in the referenced Steward patents, the disclosures of which are incorporated herein by reference, in their entirety.

As used in this document, the terms "tubing" and "hose" are deemed to be substantially equivalent, and are therefore used interchangeably.

The present invention also relates to discrete lengths of tubing or hose that have one or more characteristics that vary progressively along the lengths of tubing or hose, with at least a portion of each discrete length of tubing or hose being annealed while being axially compressed to render the portion more flexible, and while giving the portion a "memory" that causes the portion to tend to normally return to the length at which the portion was axially compressed while being annealed.

Characteristics that may vary along the discrete lengths of tubing or hose include diameter, wall thickness, pitch, strength, flexibility, stiffness, helix size and weight—while one or more of these characteristics may remain substantially constant along the same or different parts of the discrete lengths of the tubing or hose.

BRIEF DESCRIPTION OF THE DRAWINGS

These and other features, and a fuller understanding of the invention may be had by referring to the description and claims, taken in conjunction with the accompanying drawings, wherein:

DETAILED DESCRIPTION

Figure 1:
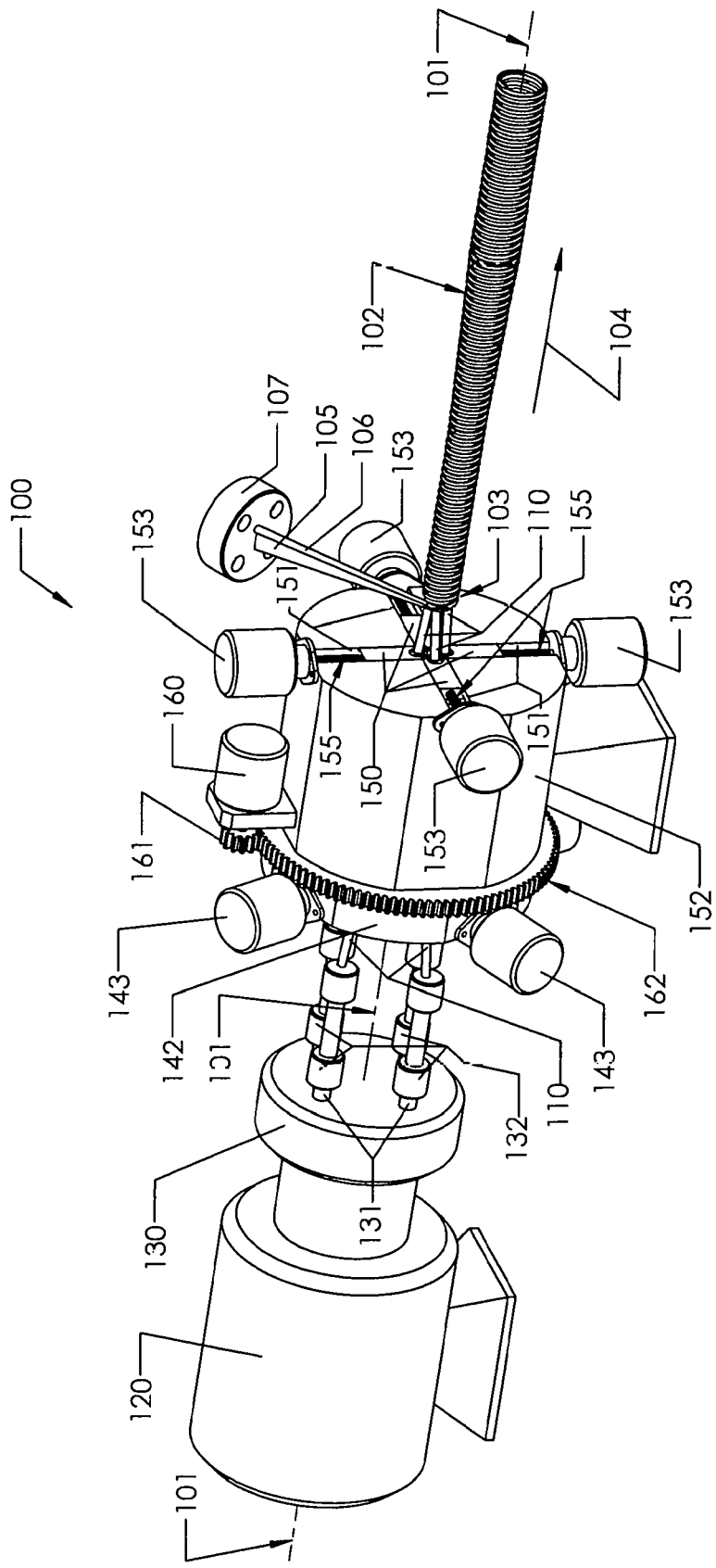
FIG. 1 is a perspective view showing front portions of an apparatus embodying features of the present invention that may carry out method features of the invention to produce helically reinforced flexible tubing or hose that embodies product features of the invention.
Figure 2:
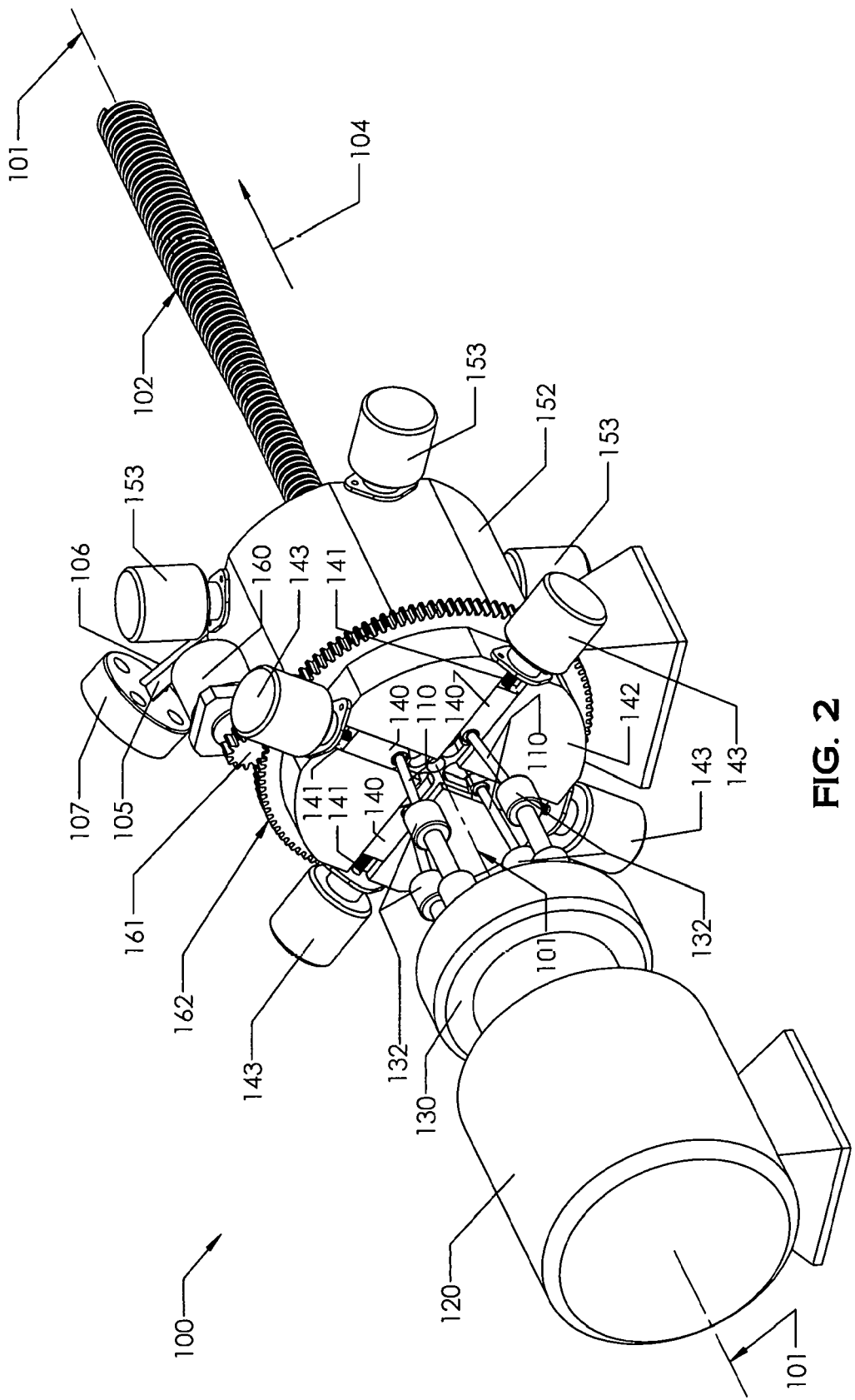
FIG. 2 is another perspective view showing rear portions of the apparatus of FIG. 1.

Referring to FIGS. 1 and 2, a tubing or hose manufacturing apparatus embodying features of the present invention is indicated generally by the numeral 100. The apparatus 100 is used to continuously produce helically reinforced tubing or hose 102 at a wrapping station 103 that is shown in FIG. 1. As the tubing or hose 102 is formed at the wrapping station 103, the newly formed tubing or hose 102 not only turns, spins or rotates about a central axis 101 but also moves along the central axis 101 (as indicated by an arrow 104) as the newly formed tubing or hose 102 departs from the wrapping station 103.

Continuous formation of tubing or hose by winding a continuously extruded web of thermoplastic material about an array of a plurality of rods 110 that are individually concurrently turned, spun or rotated in unison in a same direction of rotation is in accord with a method and apparatus that are described in the referenced two above-referenced Steward patents. As is also described in the referenced Steward patents, the rods 110 about which tubing or hose 102 is formed are canted relative to the central axis 101; and, the rods 110 converge as they extend from left to right (in FIGS. 1 and 2) toward the wrapping station 103.

As is explained in the above-referenced Steward patents, the chanting of the rods 110 assists a continuously extruded web of thermoplastic material to wind in a helically manner about the rods 110, with an edge region of each newly wrapping convolution of hot, extruded thermoplastic material slightly overlapping and promptly bonding to an edge region of an adjacent, previously wound convolution to create a continuous, contiguously extending tubing or hose wall, and with a continuous bead or rib of extruded thermoplastic material wound helically circumferentially externally around and continuously bonded to the tubing or hose wall to provide reinforcement.

The material from which the hose 102 is formed at the wrapping station 103 preferably is hot, freshly extruded thermoplastic, typically extruded from a nearby die 107 of a conventional intrusion apparatus (not shown), in a manner well known to those who are skilled in the art of intrusion.

Heated thermoplastic material extruded under pressure from the die 107 preferably includes a relatively flat, tape-like, continuous web 105 that is of substantially uniform thickness—except that integrally extruded with the web 105 may be a longitudinally extending reinforcing bead or rib 106, as is shown in the referenced Steward patents, that is typically wire-like in character so as to provide reinforcement when wound around and bonded to a wall of tubing or hose 102. A wide range of thermoplastic may form the extruded material that is helically wound at the wrapping station 103, such as, but not limited to, PVC, TPU, PP, TPE or ABS material.

It should be understood that the freshly extruded web 105 and the longitudinally extending rib or wire-like bead 106 are hot and tacky when they arrive at the wrapping station 103, and readily tend to adhere and bond promptly to each other as these materials are overlaid and helically wound or wrapped to form the tubing or hose 102. A typical manner in which the web 105 and the rib or bead 106 are overlaid and helically wrapped to form the tubing or hose 102 at the wrapping station is depicted somewhat schematically in FIG. 4, and is also described and illustrated in the referenced Steward patents.

Figure 4:
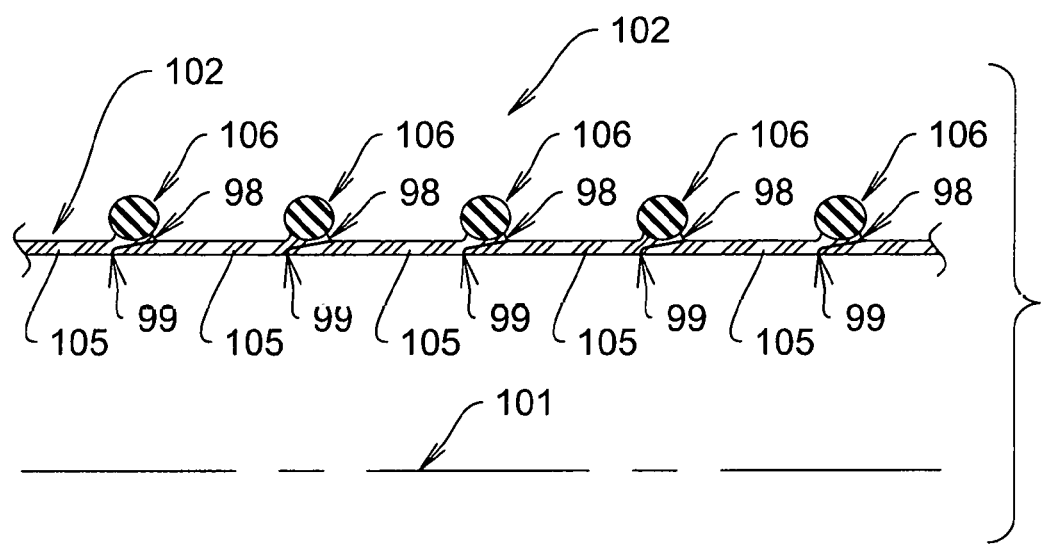
FIG. 4 is an enlarged, schematic, sectional view showing how edge portions of a web of extruded thermoplastic material overlap during helically winding to form a continuous wall of tubing or hose reinforced by a helically wound bead or rib that is integrally continuously joined with the wall of the resulting tubing or hose.

Referring to FIG. 4, it can be seen that only edge portions 98, 99 of the relatively flat, tape-like web 105 are overlaid and caused to immediately bond—and that the wall of the newly formed hose 102 produced by the helically wound web 105 is overlaid and caused to be helically reinforced by the rib or wire-like bead 106 which is wrapped or wound circumferentially around and bonded continuously and integrally to the periphery or perimeter of the wall of the newly formed hose 102.

At the wrapping station 103, the arrayed rods 110 do not turn as a group or as an array about the central axis 101. Rather, each of the identical rods 110 is supported by a separate pair of spaced-apart spherical bearings that enable the rods 110 to individually turn, spin or rotate about their individual centerline. The movable mounting of the bearings that support the rods 110 also enable the rods 110 to be moved radially relative to the central axis 101, as will be explained in greater detail shortly.

As the hot, tacky, tape-like web 105 and the wire-like bead 106 are caused to helically wrap about the array of the spinning rods 110, the speed and direction of rotation at which the outer surfaces of the rods 110 spin or turn corresponds to the direction of extrusion of thermoplastic material toward the wrapping station 103, and at least equals or exceeds the speed of the moving extrusion. Preferably, the surface speed of the turning rods 110 at least slightly pulls or stretches the extruded thermoplastic to narrow and relatively tightly wrap the extruded thermoplastic material circumferentially about the array of turning or spinning rods 110.

Figure 5:
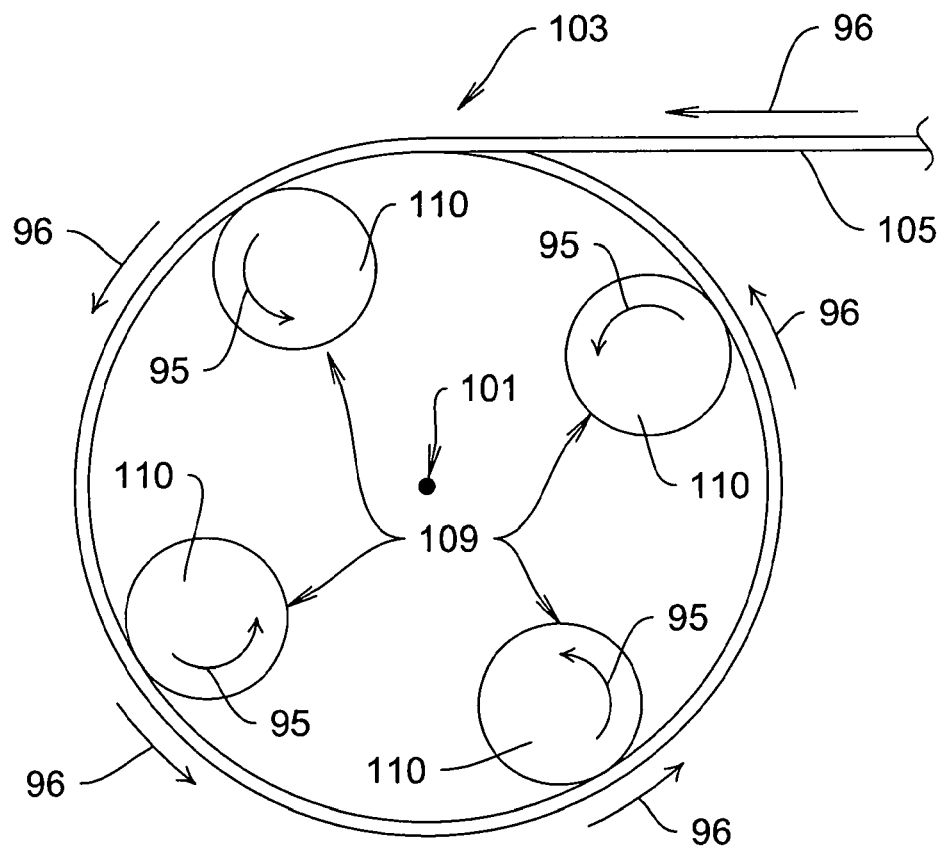
FIG. 5 also is an enlarged schematic view illustrating how a tape-like band of extruded thermoplastic is wrapped at a wrapping station in the apparatus of FIGS. 1 and 2 about a circular array of turning, rotating or spinning rods.

Schematically depicted in FIG. 5 is the manner in which the spinning rods 110 are positioned in a circular array 109 at the wrapping station 103. Also shown is how the spinning rods 110 receive the tape-like band 105 and cause the band 105 to helically wrap circumferentially around the array 109 of spinning rods 110 and bond where edge portions of the web 105 of extruded material overlap to thereby form a continuous, uninterrupted tubular wall of the hose 102. At the wrapping station 103, each of the rods 110 is identically positioned and spaced from the central axis 101. The rods 110 turn concurrently, in unison, in a same direction of rotation, as indicated by arrows 95, giving the rods 110 a surface velocity that is adjusted to match or slightly exceed the velocity at which the web 105 is fed from the extrusion die 107 located at one side of the central axis 101 in a direction generally toward the wrapping station 103. The extruded web 105 is wound or wrapped in the manner indicated by the arrows 96.

In the example illustrated by FIGS. 1, 2 and 5, the relatively close positioning of the rods 110 causes distances between adjacent ones of the spinning rods 110 to be relatively small, enabling only four of the spinning rods 110 of relatively small diameter to be used to form tubing or hose 102 of relatively small diameter. If, however, tubing or hose 102 of significantly larger diameter (not shown) is to be formed utilizing the technique described above, a larger number of the spinning rods 110, and/or spinning rods 110 of somewhat larger diameter, may be used, with adjacent ones of the rods 110 spaced equidistantly and identically positioned relative to the central axis 101, so that the tubing or hose 102 being formed does not collapse as the tape-like band 105 and the rib or wire-like bead 106 are being wrapped about the array 109 of spinning rods 110 at the wrapping station 103.

A smaller number of the spinning rods 110 and/or rods 110 of smaller size can be provided if tubing or hose 102 of a quite small diameter (not shown) is to be formed at the wrapping station 103. A larger number of the spinning rods 110 may be utilized if tubing or hose of larger diameter is to be formed at the wrapping station 103.

As those skilled in the art of extrusion will readily appreciate, the tape-like band of thermoplastic material 105 and the rib or wire-like bead 106 of extruded thermoplastic material may be extruded from entirely separate supplies (typically from separate extruders, not shown), which is particularly useful if it is desired that the materials of the tape-like web 105 and the wire-like bead 106 be formed from different thermoplastics. However, in the example depicted in the drawings, a common thermoplastic is used to form both of the materials 105, 106, and the continuous lengths 105, 106 are therefore simultaneously extruded from a single conventional extruder (not shown) through the single die 107.

By controlling the quantity and velocity of the output of molten thermoplastic from the extruder die 107, a consistent continuous supply of thermoplastic material is preferably provided forming the tape-like band 105 and the wire-like bead 106, thereby insuring that the tubing or hose 102 formed at the wrapping station 103 has a desirably uniform wall thickness with a desired type of helical reinforcement extending therearound and bonded thereto.

The apparatus 100 that supports and spins the rods 110 includes a motor 120 that powers a gearbox 130 that has an adequate number of output shafts 131 so that each output shaft 131 can spin, turn or rotate a different one of the rods 110 of the array 109. A gearbox 130 having a larger number of output shafts 131 is used if more than four spinning rods 110 are to comprise the rod array 109. Likewise, a gearbox 130 having a smaller number of output shafts 131 is used if less than four spinning rods 110 are to comprise the rod array 109.

The output shafts 131 are each connected by a flexible linkage 132 with a rear end region of a different one of the four rods 110, to cause the rods 110 to spin, while also permitting the spinning rods 110 to be movably positioned by identical rear and front slides 140, 150 (a typical one of which is indicated by the numeral 150 in FIG. 3) that carry identical rear and front spherical bearings (a typical one of which is indicated by the numeral 154 in FIG. 3) that journal rear and front portions of each of the rods 110, respectively.

As has been explained, the spinning of the rods 110 helps to cause the freshly extruded thermoplastic material that is extruded toward the array 109 of rods 110 to wrap about the rod array 109 at the wrapping station 103. By controlling speed of the motor 120 (and hence the spin speed of the rods 110), the production rate of the tubing or hose 102 is controlled to provide a resulting tubing or hose product 102 that exhibits desired characteristics.

Referring to FIG. 2, the rods 110 extend forwardly from where they connect with the linkages 132, to extend through rear spherical bearings that are carried by a set of rear slides 140 which are movable in directions radially toward and away from the central axis 101 along radially extending rear trackways 141 that are defined by a rear housing member 142. Referring to FIG. 1, the rods 110 extend still farther forwardly to where they extend through front spherical bearings 154 (FIG. 3) that are carried by a set of front slides 150 (FIGS. 1 and 3) which also are movable radially in directions toward and away from the central axis 101 along radial front trackways 151 that are defined by a front housing member 152.

As can best be seen in FIG. 2, four rear servo motors 143 are provided on the rear housing member 142 to move the four rear slides 140 radially toward and away from the central axis 101 along the four rear trackways 141 that are defined by the rear housing member 142. Each of the servo motors 143 moves a different one of the rear slides 140. Likewise, as can best be seen in FIG. 1, four front servo motors 153 are carried by the front housing member 152 to individually radially move the front slides 150 along the four front trackways 151 that are defined by the front housing member 152.

By concurrently operating the four rear motors 143 in unison, and by concurrently operating the four front motors 153 in unison, the rods 110 may be moved radially (i.e., they may be repositioned radially) while maintaining the slides 110 at equal distances from the central axis 101. By adjusting the positions of the rear and front slides 140, 150 along the rear and front radially extending trackways defined by the rear and front housings 142, 152, respectively, the portions of the spinning rods 110 about which the freshly extruded thermoplastic materials 105, 106 are wrapped at the wrapping station 103 can cause tubing or hose of smaller or larger diameter to be formed at the wrapping station.

Preferably, the rear and front slides 140, 150 are of identical configuration, as are the rear and front spherical bearings that are carried by the slides 140, 150. Likewise, the rear and front motors 143, 153 are identical, as are the output shafts of the motors 143, 153 that connect with and cause movement of the rear and front slides 140, 150 along the rear and front radially extending trackways 141, 151, respectively.

Figure 3:
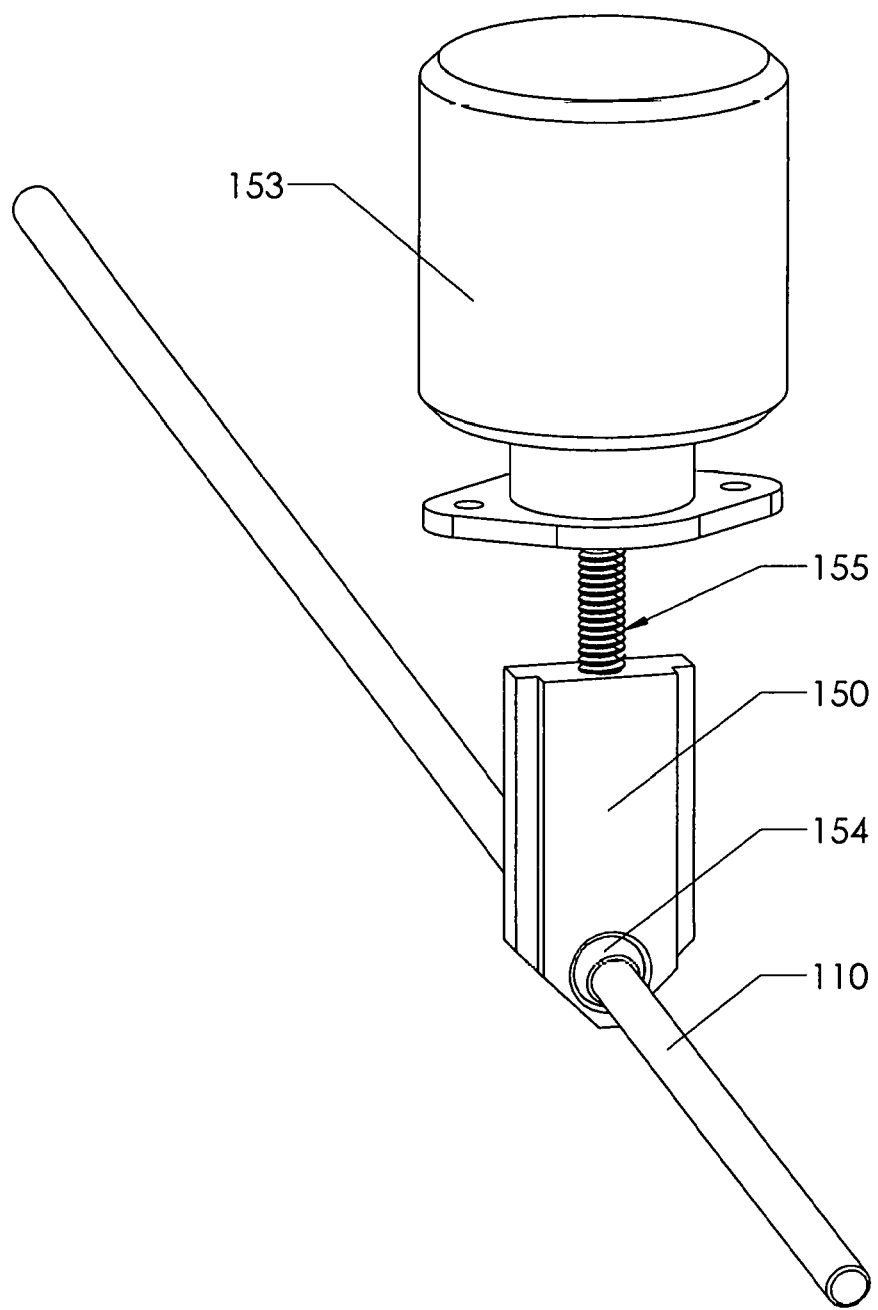
FIG. 3 is an enlarged perspective view of selected components associated with the support and positioning of one of a plurality of spinning rods arranged in an array within the apparatus of FIGS. 1 and 2.

A typical one of the slides 150 is shown in FIG. 3 carrying a typical spherical bearing 154. A typical one of the motors 153 also is shown in FIG. 3 as having an output shaft 155 that is threaded into an associated one of the slides 150. Rotation of the output shaft 155 in one direction causes the slide 150 to move toward the central axis 101. Rotation of the shaft 155 in the opposite direction causes the slide 150 to move in an opposite direction away from the central axis 101.

As can be seen by comparing the positions of the rear and front motors 143, 153 in FIGS. 1 and 2, the rear and front trackways 141, 151 that are defined by the rear and front housings 142, 152, respectively, are typically not aligned. Stated in another way, the rear trackways 141 along which each of the rear slides 140 move are, in essence, "canted" relative to the front trackways 151 along which each of the front slides 150 move. The extent to which these rear and front trackways 141, 151 are canted held out of alignment is determined by a servo motor 160 carried by the front housing member 152, which causes the rear housing member 142 to turn about the central axis 101 (to a small and limited extent) relative to the front housing member 152 (which is fixed and therefor does not turn about the axis 101).

The motor 160 drives an output gear 161 that meshes with and drives a much larger gear 162 that rings and is connected to the rear housing member 142. Rotation of the output gear 161 of the motor 160 causes the large gear 162 to turn slightly about the central axis 101, thereby causing the four planes in which the rear trackways 141 extend to turn either relatively closer into alignment with, or relatively farther out of alignment with, the four planes in which the front trackways 151 extend. By controlling the extent to which the rear trackways 141 are canted relative to the front trackways 151, the extent to which edge portions 98, 99 of the tape-like band 105 overlap (as shown somewhat schematically in FIG. 4) is controlled. Stated in another way, the helical wrapping of the tape-like band 105 and the wire-like bead 106 is caused to take place, and its character is controlled by the servo motor 160 which causes the rods 110 to be canted relative to the center axis 101.

A significant feature of the present invention resides in the realization that the needed canting of the rods 110 that define the wrapping station 103—the rods 110 about which extruded thermoplastic material is wound—can be nicely controlled by simply relatively turning the front and rear housing members 152, 142 about the center axis 101. Although the referenced Steward patents recognize the need for canting rods about which extruded thermoplastic is wound, the Steward patents in no way teach or suggest that the needed rod canting can be provided simply by relatively turning two housing members that support front and rear sets of bearings that journal the rods for rotation.

Nor do the referenced Steward patents teach or suggest that needed rod canting can be adjusted or modified by relatively turning two housing members about a central axis along which newly formed hose travels as it exits a wrapping station defined by the spinning rods, or that the pitch of newly formed hose can be changed by relatively turning front and rear housings that carry front and rear bearings that support front and rear portions of the array of spinning rods that define a wrapping station.

Figure 6:
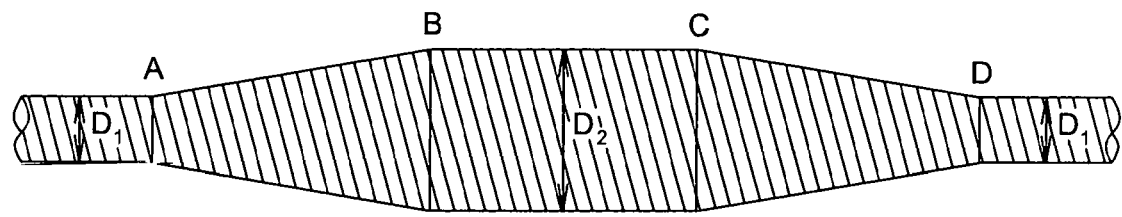
FIG. 6 is a side elevation's view of a length of tubing or hose that has a straight-walled or truncated conical taper that transitions from a relatively smaller $D_1$ diameter to a relatively larger $D_2$ diameter, and then has a straight-walled or truncated conical taper that transitions back from the $D_2$ diameter to the $D_1$ diameter, and is transversely cut or severed mid-way along spaced, constant diameter portions, regions or reaches that are of the $D_1$ and $D_2$ diameters.
Figure 7:
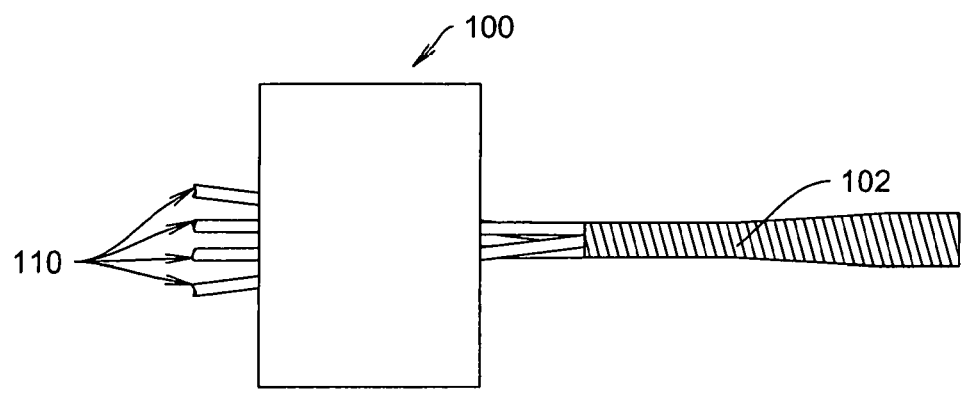
FIG. 7 is a simplified side elevation's view showing a portion of the apparatus of FIGS. 1 and 2 with rods that define a wrapping station set to form a tubing or hose portion, region or reach of relatively smaller diameter.
Figure 8:
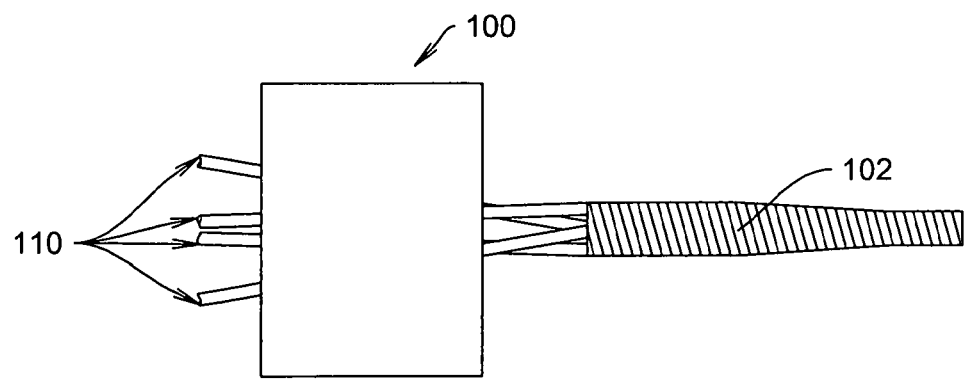
FIG. 8 is a simplified side elevation's view similar to FIG. 7, but showing rods that define a wrapping station set to form a tubing or hose portion, region or reach of relatively larger diameter.

Referring to the example illustrated in FIG. 6, a hose length 102 that exhibits a desired straight or conical taper that transitions from a relatively smaller diameter $D_1$ at point A to a relatively larger diameter $D_2$ at point B can be formed by first setting the rods 110 as illustrated in FIG. 7 to form the relatively smaller diameter $D_1$, and then gradually and progressively moving the rods 110 until they assume the configuration depicted in FIG. 8 to form the relatively larger diameter $D_2$ to provide a hose length such as is shown in FIG. 6 as extending from points B to C. The rods 110 are then preferably moved gradually and progressively back to the configuration depicted in FIG. 7 to form a reverse of the A to B taper, yielding a taper that extends from points C to D, followed by the production of a length of the relatively smaller diameter hose $D_1$ starting at point D.

When the resulting hose shown in FIG. 6 is cut in the two indicated places mid-way along the lengths that exhibit $D_1$ and $D_2$ diameters, two identical hoses are provided, each of which includes one of the depicted conical tapers. This technique of forming a single length of hose that includes a back-to-back sequence of two desired tapers (from a first diameter to a second, and then from the second diameter back to the first diameter, with the two tapered half lengths of hose then being cut apart), can be used repeatedly, yielding an extremely efficient way to produce hoses that incorporate a desired type of single taper.

Figure 9:
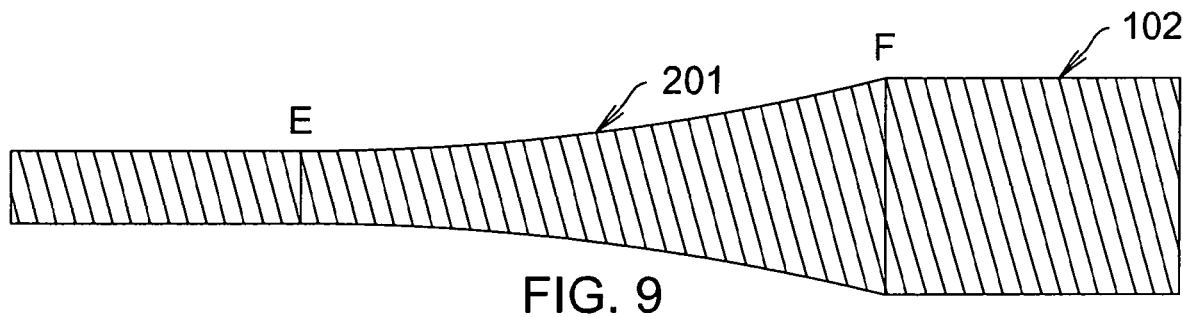
FIG. 9 is a side elevation's view of a length of tubing or hose that includes a concavely curved or tapered portion, region or reach transition's between tubing or hose portions, regions or reaches of relatively smaller and relatively larger diameters.
Figure 10:
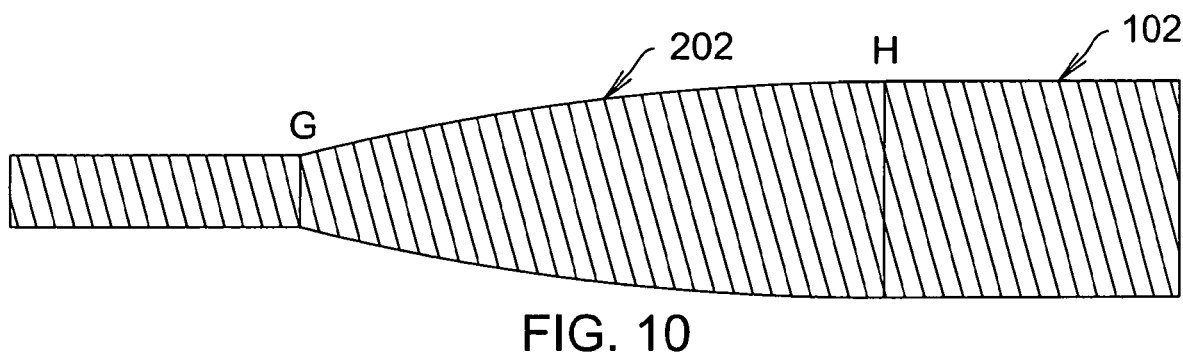
FIG. 10 is a side elevation's view of a length of tubing or hose that includes a convexly curved taper transition's between hose portions, regions or reaches of relatively smaller and relatively larger diameters.
Figure 11:
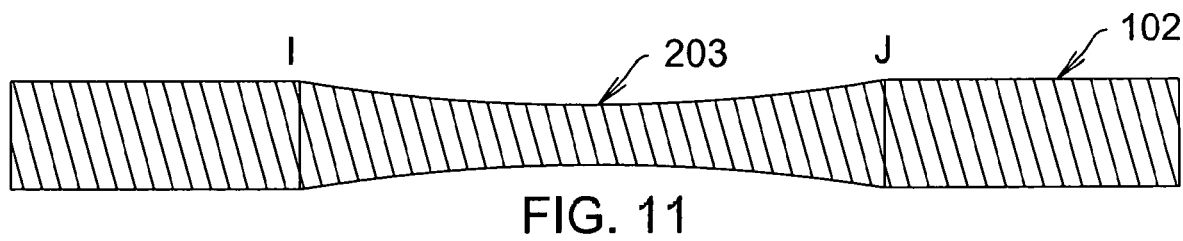
FIG. 11 is a side elevation's view of a length of tubing or hose that includes a concave portion, region or reach transition's between two tubing or hose portions, regions or reaches of equal and relatively large diameter; and, FIG. 12 is a side elevation's view of a length of tubing or hose that includes a convex portion, region or reach transition's between two tubing or hose lengths of relatively equal and relatively small diameter.
Figure 12:
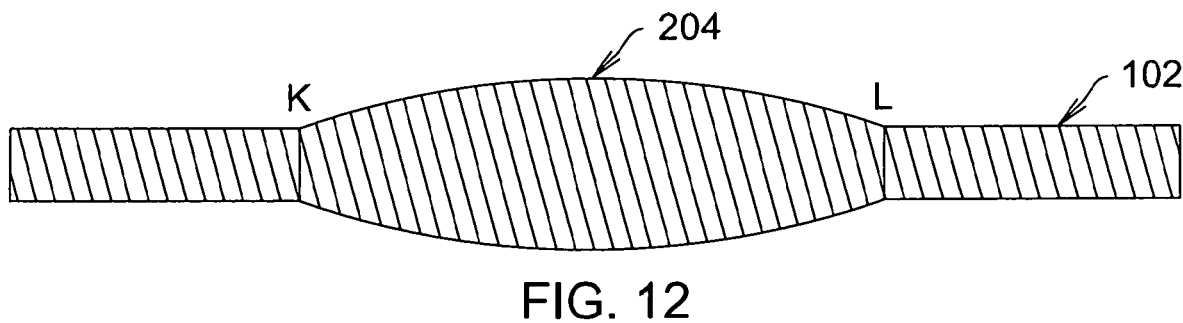

The production of hose lengths that incorporate other types of tapers can also be produced using the adjustable rods 110 to define a wrapping station 103 where hose 102 of a desired configuration is formed. By way of example, FIG. 9 shows a hose length 102 that incorporates a concavely curved taper 201 that extends between points E and F, to transition between a relatively smaller diameter and a relatively larger diameter. In a similar vein, FIG. 10 shows a hose length 102 that incorporates a convexly curved taper 202 that extends between points G and H, to transition between a relatively smaller diameter and a relatively larger diameter. FIG. 11 shows how a concave reach of hose 203 can be provided to transition between two hose lengths of substantially equal diameter; and, FIG. 12 shows how a convex reach of hose 204 can be provided to transition between two hose lengths of substantially equal diameter.

To control the apparatus 100, a conventional servo motor controller (not shown) is preferably provided that not only regulates the speed at which the motor 120 turns the rods 110, but also the variable settings of the servo motors 143, 153 and 160, and the parameters of operation of an extruder that extrudes the thermoplastic materials 105, 106 emitted from the extrusion die 107 toward the rods 110 at the wrapping station 103. To form a tapered hose such as is depicted in FIG. 6, the parameters needed to produce the relatively smaller diameter hose $D_1$ at the wrapping station 103 are locked into the controller, as well as the parameters needed to produce the relatively larger hose $D_2$, together with such information as is needed to define the taper that transitions between the two diameters $D_1$ and $D_2$, and such parameters as position the rods 110 to produce a hose length exhibiting a desired pitch.

The term "pitch," as it is used in conjunction with the formation of helically wrapped tubing or hose, means the distance from a particular point on one helix or wrap, to the same particular point on an adjacent helix or wrap—for instance, the distance from the center of one helix or wrap to the center of an adjacent helix or wrap. If the rods 110 were not canted at all, material 105 from the extruder die 107 would wrap atop itself time and again instead of helically wrapping to form the hose 102. A small amount of canting or angulation of the rods 110 will cause the resulting helically wrapped hose 102 to have a tight pitch of short length. A larger amount of canting or angulation of the rods 110 will produce a helically wrapped hose 102 having a wider pitch of longer length.

To form a helically wrapped tubing or hose 102 of a certain diameter that has a given pitch length will require a certain angulation or canting of the rods 110. Because the spacing of the rods 110 from the central axis 101 (at the wrapping station 103) determines the diameter of the hose 102 that is being produced, the rods 110 are first positioned so that a hose 102 is produced that is found to have a desired diameter.

Once the apparatus 100 is producing hose 102 of a desired diameter, the angulation or canting of the rods 110 is adjusted (by using the motor 160 to turn the rear housing 142 relative to the front housing 152) to give a rod angulation or canting that provides the resulting hose 102 with a desired pitch length.

To form a taper that progressively increases or decreases the diameter of the hose 102 being produced, the rods 110 are progressively moved radially inwardly or radially outwardly to modify the diameter of the resulting hose 102 in a desired manner. However, if the pitch of the hose 102 being produced is to be maintained while a taper in diameter is progressively being formed, it is also necessary to progressively alter or adjust the angulation or canting of the rods 110. This is because a longer amount of time and a longer length of extruded material 105 are needed to form each wrap that is of a progressively longer length as the diameter of the hose 102 being produced is being progressively increased—and because a shorter amount of time and a shorter length of extruded material 105 are needed to form wraps that are of progressively shorter length as the diameter of the hose 102 being produced is progressively diminished.

A smaller angulation or canting of the rods 110 is needed to provide a given pitch when forming a larger diameter of tubing or hose 102; and a larger angulation or canting of the rods 110 is needed in order to provide the same given pitch when forming a smaller diameter of tubing or hose 102. When a taper is being formed that increases the diameter of the hose 102, the angulation or canting of the rods 110 (that is being progressively adjusted by the motor 160) must decrease if the resulting hose 102 is to have a constant pitch; and, when a taper is being formed that diminishes the diameter of the resulting hose 102, the angulation or canting of the rods 110 must increase if the resulting hose 102 is to have a constant pitch.

In the formation of some lengths of the hose 102, it is desired that pitch length be progressively altered to either increase or decrease. The motor 160 can be progressively used to effect such progressive changes in hose pitch. One reason why a change of pitch may be desired is that a tighter or shorter pitch length can provide a thicker, stronger, stiffer, more fully reinforced hose 102 that can handle increased pressure or a vacuum of greater intensity. Another reason why a change of hose pitch may be desired is to progressively change one or a selection of characteristics such as hose thickness, hose strength, hose stiffness or hose flexibility, hose weight, and other such characteristics that may be progressively changed along the length of a hose 102 being produced by the apparatus 100. For example, a relatively small hose diameter might be selected having characteristics of one type for one hose region, and another region of the same hose might be formed with a larger diameter and different characteristics.

Once the system settings have been "trimmed" by the operator to give the desired end product, a hose will be automatically produced in a continuous cycle first giving a hose (as shown in FIG. 6 hereof) that exhibits a constant first relatively smaller diameter $D_1$ having tapered length transitioning from the relatively smaller diameter $D_1$ to the relatively larger diameter $D_2$, and then a tapered length transitioning back from the relatively larger diameter $D_2$ to the relatively smaller diameter $D_1$.

The tapers or changes in hose diameter that are made along particular hose lengths or reaches may be conical in nature, or may conform to other configurations that provide relatively smooth diameter changes. Lengths or reaches of hose that are of substantially constant diameter may also be provided, as a design for a particular hose application may dictate. Hoses of desired constant diameter, or of a desired tapering diameter that changes slowly or rapidly over long or short reaches or lengths can be created, to provide an essentially limitless combination of hose diameters and taper angles.

What is not shown by FIGS. 6 and 9-12, but will be readily apparent to those skilled in the art, is that substantially any of the tapered forms that are shown may be combined, as a hose designer may deem appropriate for a particular application.

The process of the present invention works well with substantially any traditional material from which thermoplastic hoses commonly are produced—examples being TPC-ET, flexible polypropylene, polyethylene, polyurethane and the like. In a dual extruder arrangement where the tape material used to form the body of a hose and the helical reinforcing material are separately extruded, the helix material would typically be a harder material relative to the material used to form the tape-like wall portion of the flexible hose being manufactured.

The flexible hose formed herewith can, for example, have a hose wall defined by a thin, narrow, elongate web formed from PVC, TPU, PP, TPE or ABS material, and can, for example, employ a helical reinforcing spiral that is formed from PVC, TPU, PP, TPE or ABS material.

Textiles can be substituted for the wall-forming tape-like material, and a coated or uncoated wire can be used to form the reinforcing helix of the hose being manufactured. Any color or additive can be added to the plastic to give custom properties or appearance.

As is well known in the art of hose production, a so-called "crush cuff" of substantially uniform diameter can be provided where newly produced hose lengths are to be severed, thus providing newly produced hose lengths with regions that are well suited to join or mate with existing fittings or rigid conduits, which can be held in place by means of friction or through the use of any of a wide variety of known hose clamps and other mechanical contrivances. A typical cuff such as can be provided on a length of hose produced using techniques of the present invention is indicated by the numerals 18a and 18b in FIG. 4 of U.S. Pat. No. 7,014,449 issued Mar. 21, 2006 to Mark Woelfel, the disclosure of which is incorporated herein by reference. The referenced Steward patents also show the positioning of a roller 44 near where extruded thermoplastic material is wound about a plurality of spinning rods—a roller 44 that can be used to periodically flatten a reinforcing bead or rib to periodically provide cuffs that have no upstanding reinforcing bead or rib, and that may therefore be joined easily with existing fittings and the like.

If desired, features of the present invention may be practiced by replacing the smooth rods 110 that spin (about which the tape-like material is wound to form the flexible wall of the hose at the wrapping station 103) with contoured shafts that create hose profiles that are designed to increase the stretch ratio of the resulting hose.

In accordance with the invention described in an earlier-filed application Ser. No. 12/799,263 filed Apr. 21, 2010 by Martin E. Forrester et al entitled FLEXIBLE, STRETCHABLE, CRUSH RESISTANT HOSE WELL SUITED FOR MEDICAL APPLICATIONS, and its predecessor applications, the disclosures of all of which are incorporated herein by reference, in their entireties), tubing or hose lengths, or portions, regions or reaches thereof that are produced in accordance herewith may be compressed and annealed to impart ultra-flexible reaches with stretch ratios that are increased. Such stress-relieved hose reaches are particularly desirable in medical applications where undesirably stiff hoses may cause breathing masks to leak or move out of place, or may cause connections between tubing or hoses or components of tubing or hose circuitry to disconnect.

Utilizing features of the present invention, hose can also be manufactured with multiple starts, where two or more helical beads are used along with a tape-like band that is wide enough to span the entire width of the desired profile plus the necessary extra width to bond the profile beneath or overlying the helix to create a smooth hose. Multiple starts also allow the hose to be manufactured more quickly as the hose progresses down the length of the spinning rods two or more pitches per hose revolution. Further, multiple starts also allows for different materials to be used in the helical portion for color coding, or to provide other unique physical properties.

In some embodiments of the invention, multiple start helices (not shown) can be utilized (i.e., by using plural, side-by-side, simultaneous extrusions of hot tape-like bands of thermoplastic that wrap side-by-side so that overlapping edge portions of adjacent tape-like bands bond to form a hose wall), thereby resulting in a production speed that is increased by a factor equal to the number of multiple starts per hose revolution.

In some embodiments of the invention, the rate at which the rods are spun, turned or rotated is adjusted so that the angular velocity of the outer surfaces of the rods is preferably maintained at not less than the velocity at which hot thermoplastic material is extruded toward the wrapping station. In accordance with other embodiments, the surface speed of the outer surfaces of the rods may be adjusted to achieve a desired stretching or "draw down" of the molten tape-like band and/or the wire-like bead of the hot, freshly extruded thermoplastic so as to cause the newly formed hose to exhibit desired dimensions such as a particular desired thickness, or to exhibit desired characteristics of strength as chains of molecules become suitably oriented during formation of the newly formed hose wall and its helical reinforcement.

The present invention preferably provides an electromechanical system that repositions the spinning rods as hose is formed, to thereby create tapered lengths or reaches of hose, or hose that has tapered lengths or reaches between substantially straight lengths or reaches of substantially constant diameter that typically may be of differing diameters. The process used can be continuous in nature, repeating at pre-determined intervals to create hose with one starting diameter and length, followed by a tapered section of desired length, followed by an ending diameter and length—whereafter the process is reversed to create substantially the same piece of hose that transitions from the ending diameter and length to the starting diameter and length, with cuttings being made at locations selected to give two exactly identical pieces of hose. In much the same manner, the a hose being manufactured can be severed at various pre-determined positions to create desired discrete hose lengths consisting of one or more straight or constant diameter sections with one or more tapered sections therebetween, as a particular hose design dictates.

Among features of the present invention (that are in no way taught or suggested by the prior art) is an arrangement for movably supporting the individual rods in bearings that not only permit the rods to turn, spin or rotate, but also permit the rods to be concurrently radially moved continuously and progressively during formation of at least a continuous portion, region or reach of a length of thermoplastic tubing or hose that is being formed at a wrapping station, so that at least the resulting portion, region or reach of tubing or hose changes substantially continuously and progressively in diametrical size—so the resulting portion, region or reach of tubing or hose tapers as may be desired, for example to provide an appearance that is of truncated conical shape, or a configuration that is characteristically concave, convex or bulbous in appearance, or changes in some other way from one diameter to a different diameter.

As those skilled in the art will readily appreciate, the methods or techniques described herein can be used to provide tubing or hose lengths that have portions, regions or reaches of constant diameter (by maintaining the positions held by the rods such as is described in the two referenced Steward patents), and that have portions, regions or reaches that progressively change in diametrical size (by progressively moving the rods so that their positions relative to an imaginary center axis about which newly formed hose moves away from a wrapping station). Causing the rotating, turning or spinning rods of the rod array to be spaced farther from the center axis will cause hose being produced to have a relatively larger diameter or size. Causing the rods of the array to be spaced closer to the center axis will cause the tubing or hose being produced to have a relatively smaller diameter or size.

The method just described can be used to continuously produce reaches or lengths of helically reinforced flexible tubing or hose that exhibit a plurality of differing diameters, with transitional portions, regions or reaches that smoothly connect the differing diameters by means of conical tapers or tapers that feature other relatively smooth, continuous and progressive, curved or perhaps even elliptical areas of transition.

The heated, freshly extruded tape-like and wire-like thermoplastic materials that are helically wrapped to form a helically reinforced flexible hose in accordance with some embodiments of the invention 1) may be concurrently extruded from a single extrusion apparatus using a single extrusion die as a unified band of thermoplastic, 2) may be co-extruded from a single extrusion die using two or more extruders to provide thermoplastic materials to form a hose comprised of multiple materials having different properties (such as different stiffness, fatigue resistance, chemical resistance, or other physical properties), or 3) may be simultaneously extruded from separate extruders through separate extrusion dies so that the wall and reinforcing helix of the resulting hose are comprised of different materials that preferably are caused to bond as they are laid together at and move away from the stationary array of spinning rods at a wrapping station.

In accordance with some embodiments of the invention, continuous, pre-extruded tapes, fabrics, wire-like beads and the like can be utilized if they are heated before being brought together and wrapped about an array of spinning rods as described above, with heat being provided by a conventional external heat source (not shown) such as hot air to render bondable the materials that form a continuous tubing or hose wall and a continuous reinforcing helix bonded continuously to the hose wall. In some embodiments, adhesives also may be used to create a bond between materials that are wrapped about an array of spinning rods such as is described above to create a desired tubing or hose profile that spins about an imaginary central axis as it moves away from a wrapping station (as do all hose embodiments formed at a wrapping station defined by an array of spinning rods in accordance herewith).

Although the invention has been described in its preferred form with a certain degree of particularity, it is understood that the present disclosure of the preferred form has been made only by way of example, and that numerous changes in the details of construction and the combination and arrangement of parts and techniques may be resorted to without departing from the spirit and scope of the invention as hereinafter claimed. It is intended to protect whatever features of patentable novelty that exist in the invention disclosed.

What is claimed is:

1. A length of helically reinforced flexible hose comprising:
   a first portion of a hose wall that increases in diameter from a smaller diameter end of the first portion to a larger diameter end of the first portion;
   a second portion of the hose wall having a larger diameter end that is formed integrally with the larger diameter end of the first portion of the hose wall, and which decreases in diameter from the larger diameter end of second portion to a smaller diameter end of the second portion; and a continuous reinforcing rib helically wrapped around the first and second portions of the hose wall, wherein:

the hose wall and reinforcing rib are continuously formed from continuously extruded thermoplastic material helically circumferentially wrapped at a wrapping station around an array of concurrently turning bearing-supported rods that are canted relative to an imaginary central axis;

positions of the rods relative to the central axis are progressively altered during formation of the first portion to cause the first portion to exhibit a first progressive continuous change in hose diameter between the smaller end and the larger end of the first portion; and the positions of the rods relative to the central axis are progressively altered during formation of the second portion to cause the second portion to exhibit a second progressive continuous change in diameter that is opposite to the first progressive continuous change in diameter between the larger end and the smaller end of the second portion.

2. The length of hose of claim 1 wherein the first portion at least partially coincides with the second portion.

3. The length of hose of claim 1 wherein at least some of the lengths of the first and/or second portions have been axially compressed and annealed to relieve stress and to enhance flexibility thereof.

4. The length of hose of claim 1 wherein the length of the first portion does not include any part of the length of the second portion.

5. The length of hose of claim 1 comprising a third portion of substantially constant diameter.

6. The length of hose of claim 1 wherein substantially the entire length of the hose has a hose wall formed by wrapping a tape-like web of the thermoplastic material at the wrapping station, and the hose wall of the first portion has a substantially uniform thickness resulting at least in part from progressively altering a speed at which the rods are concurrently turned while the relative positions of the rods are being progressively altered, with the speed of rotation of the rods being diminished as hose diameter being produced is increased.

7. The hose of claim 1 wherein another characteristic of the first portion progressively changes, and the other characteristic is selected from a group consisting of wall thickness, pitch, strength, flexibility, stiffness, helix size, weight, flow velocity and flow pressure.

8. The hose of claim 1 wherein the first progressive continuous change in diameter of the first portion yields a hose taper of progressively diminishing diameter, and the second progressive continuous change in diameter of the second portion yields a hose taper of progressively increasing diameter.

9. The hose of claim 1 wherein the first progressive continuous change in diameter of the first portion yields a concave taper or a convex taper.

10. The hose of claim 1 wherein the first progressive continuous change in diameter of the first portion yields a bulbous form of taper.

11. The hose of claim 1 wherein the first progressive continuous change in diameter of the first portion provides a progressive transition from a first hose diameter to a different second hose diameter.

12. The hose of claim 1 wherein the extruded thermoplastic material helically circumferentially wrapped at the wrapping station to form the hose wall includes a tape-like web consisting of PVC, TPU, PP, TPE or ABS material, and the reinforcing rib is helically wrapped around the wall; and with the reinforcing rib wrapped around the hose wall consisting of PVC, TPU, PP, TPE or ABS material.

\* \* \* \* \*